United States Patent [19]

Okamoto et al.

[11] Patent Number: 4,465,845

[45] Date of Patent: * Aug. 14, 1984

[54] HIGH PRESSURE SYNTHESIS OF SULFUR-SELENIUM FULVALENES

[75] Inventors: Yoshiyuki Okamoto, Ft. Lee, N.J.; Piotr S. Wojciechowski, Lodz, Poland

[73] Assignee: Koppers Company, Inc., Pittsburgh, Pa.

[*] Notice: The portion of the term of this patent subsequent to Sep. 6, 2000 has been disclaimed.

[21] Appl. No.: 372,058

[22] Filed: Apr. 26, 1982

[51] Int. Cl.$^3$ .......................................... C07D 343/00
[52] U.S. Cl. ...................................... 549/30; 549/35; 549/39
[58] Field of Search .............................. 549/30, 39, 35

[56] References Cited

U.S. PATENT DOCUMENTS

| | | | |
|---|---|---|---|
| 3,876,662 | 4/1975 | Hartzler | 549/39 X |
| 4,312,992 | 1/1982 | Green | 549/39 |
| 4,402,875 | 9/1983 | Okamoto et al. | 260/239 R |

FOREIGN PATENT DOCUMENTS 2739584 6/1978 Fed. Rep. of Germany .

OTHER PUBLICATIONS

Narita et al., International Journal of Methods in Synthetic Organic Chemistry, No. 7, (1976), pp. 425-488.
Hartzler, J.A.C.S., vol. 92, No. 5, (1970), pp. 1412-1414.

*Primary Examiner*—Richard L. Raymond
*Attorney, Agent, or Firm*—Donald M. MacKay; J. Timothy Keane; Herbert J. Zeh, Jr.

[57] ABSTRACT

A process is disclosed for one-step preparation of sulfur-selenium fulvalenes by reaction of an acetylenic compound with carbon selenide sulfide or with a mixture of carbon diselenide and carbon disulfide under pressures of at least about 1,000 atmospheres. Fulvalene compounds made by the process are characterized in having at least one sulfur atom and at least one selenium atom in the ring structure of the fulvalene compound. Substituted diselenadithiafulvalenes made by this process are precursors to very pure diselenadithiafulvalene which is useful in preparing charge-transfer salts.

12 Claims, No Drawings

HIGH PRESSURE SYNTHESIS OF SULFUR-SELENIUM FULVALENES

BACKGROUND OF THE INVENTION

1. Field of the Invention

Preparations of sulfur-and-selenium-containing fulvalenes are well known. Of particular interest herein is a one-step method for synthesis of substituted sulfur-and-selenium-containing fulvalenes from reactions of an acetylenic compound with sulfide-and-selenide starting materials under high pressure conditions.

2. State of the Art

Recent findings of the unusual electronic properties of complexes of certain sulfur-and-selenium-containing fulvalenes have generated increased interest in new synthetic routes for preparation of these fulvalene compounds. Certain fulvalene compounds having sulfur and selenium atoms in the fulvalene rings can be used to prepare crystalline charge-transfer salts. For example, in IBM German Offen. No 2,739,584 (1978), there is described a charge-transfer salt comprised of dithiadiselenafulvalene and tetracyano-p-quino-dimethane. Such salt, in which the fulvalene compound is characterized as the electron-donor cation, exhibits metallic properties over a wide temperature range and reportedly has electrical conductivity among the highest of known organic materials.

The superior electrical properties of these salts, so-called "organic metals", make the salts particularly likely candidates for many solid-state or physical-electronics applications. In such applications, materials of very high purity are usually required. Known preparations of sulfur-and-selenium fulvalenes and substituted sulfur-and-selenium fulvalene compounds involve complicated multi-step synthetic routes which typically produce these fulvalene compounds in low yields or in relatively impure form.

One lengthy method for making fulvalene compounds containing sulfur and selenium in the five-membered ring system is described in U.S. Pat. No. 3,941,809 to Kaplan et al. These fulvalene compounds are prepared by a multi-step method involving firstly reduction of a sulfur-and-selenium-containing five-member ring organic halide to its partially-hydrogenated derivative, which derivative is reacted with anhydrous fluoboric acid to provide a fluoborate, which fluoborate is then deprotonated in the presence of an alkyl tertiary amine to yield a fulvalene compound containing two sulfur and two selenium atoms.

In U.S. Pat. No. 4,028,346 to Engler et al, a two-step synthesis is described for preparation of sulfur-selenium fulvalenes. This method involves reacting sodium acetylide with carbon diselenide in the presence of sulfur to provide 1,3-thiaselenole-2-selone. A subsequent coupling reaction of this selone compound in the presence of trimethylphosphite produces dithiadiselenafulvalene in an unreported yield. In a later publication, however, Lakshmikantham and Cava [J. Org. Chem., 45, 2632 (1980)] report that the Engler type two-step synthesis provides an overall yield of dithiadiselenafulvalene of less than one percent. This later publication then describes an improved route for synthesis of dithiadiselenafulvalene by first converting 1,2,3-selenadiazole to 1,3-thiaselenole-2-thione, which thione is then converted by conventional methods to 1,3-thiaselenole-2-selone and then by coupling reaction to dithiadiselenafulvalene. Overall yield of this fulvalene is only about 24 percent, however.

SUMMARY OF THE INVENTION

Sulfur-and-selenium-containing fulvalene compounds are prepared by subjecting a mixture of reactants to a pressure of at least about 1,000 atmospheres, those reactants comprising compounds providing a selenide constituent, a sulfide constituent and an acetylenic moiety. The selenide and sulfide constituents may be provided by a single compound, such as carbon selenide sulfide, or by a plurality of compounds, such as a mixture of carbon diselenide and carbon disulfide. The acetylenic moiety may be provided by a compound as expressed by the general formula $ZC{\equiv}CZ$ wherein the Z substituents are independently selected from the set consisting of the following members:

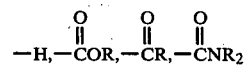

with the proviso that both Z substituents cannot be hydrogen at the same time. Thus the starting compound containing the acetylenic moiety is further characterized by at least one of the Z substituents being an electron-withdrawing substituent, inasmuch as each of the illustrated structures, other than hydrogen, is an electron-withdrawing substituent. For each of the illustrated electron-withdrawing substituents, R may be hydrogen or may be selected from alkyl, aryl and alkaryl groups of up to about 12 carbon atoms. Where R is hydrogen in the illustrated structural groups, the Z substituent will be carboxyl group, aldehyde group, and amide group, respectively. It is understood that in the amide group structure, each of the two R groups may be hydrogen, alkyl or aryl substituents, or any combination thereof, so as to embrace primary, secondary and tertiary amido groups. A starting compound or compounds must be selected to provide the selenide and sulfide constituents and must react with the compound containing the acetylenic moiety such that the fulvalene compound of the reaction product contains both sulfur and selenium atoms in the fulvalene ring structure.

A principal advantage of the present invention is that sulfur-and-selenium-containing fulvalenes are provided by a one-step reaction, as compared to known synthetic routes requiring complicated multi-step reactions. Moreover, the process of the invention may be carried out in the absence of catalyst. Inasmuch as contaminating catalysts are not required in the present process, substituted fulvalene compounds of exceptional purity can be prepared. Such compounds are useful as precursors to obtaining very pure sulfur-and-selenium-containing fulvalenes. Moreover, synthesis of troublesome by-products is less likely in the single-step process of the invention as compared to multi-step preparations.

DETAILED DESCRIPTION OF THE INVENTION

The terms "high pressure synthesis" and "high pressure reactions" as used herein are intended to describe preparation of fulvalene compounds by subjecting certain reactants to a pressure of at least about 1,000 atmospheres for a time and at a temperature sufficient to form fulvalene compounds. The terms "fulvalene compound", "sulfur-selenium fulvalene compound", "sulfur-and-selenium-containing fulvalene", and "Z" group-substituted analogues thereof, are used to describe products derived from or made in accordance with the process of the invention. These products contain the basic structural configuration depicted in formula I:

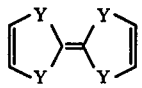 (I)

wherein "Y" is a sulfur or selenium atom, with the proviso that the fulvalene compound contain within its ring structure at least one sulfur atom and at least one selenium atom. The term "ring structure" as used herein is intended to describe a system consisting of two five-membered rings joined together by a double bond. The requirement of at least one sulfur atom and at least one selenium atom being present in the fulvalene ring structure is thus satisfied by these two atoms being contained in one ring or by one ring containing a sulfur atom and the other ring containing a selenium atom.

Such fulvalene compounds may be prepared by processes comprising the step depicted generally in equation II for making substituted fulvalene compounds, as follows:

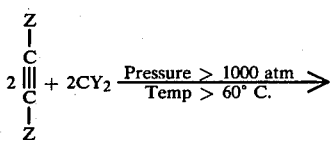 (II)

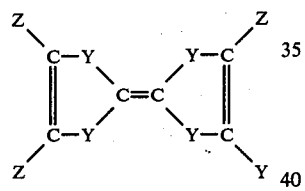

wherein the Z groups are substituents as defined before. Expected substituted fulvalene compound reaction products will be found as both cis- and trans-isomers, with respect to the "Z" substituents.

The starting material $CY_2$, wherein Y is sulfur or selenium, includes compounds such as carbon diselenide ($CSe_2$), carbon disulfide ($CS_2$), and carbon selenide sulfide (CSeS). The starting material $CY_2$ must be selected such that at least one selenium atom and at least one sulfur atom are contained within the rings of the fulvalene compound reaction product. Typical reaction products may include fulvalene compounds having, with the two rings considered together, one selenium atom and three sulfur atoms such as a trithiaselenafulvalene, or three selenium atoms and one sulfur atom such as a triselenathiafulvalene, or two selenium atoms and two sulfur atoms such as a dithiadiselenafulvalene.

Trithiaselenafulvalene, having the empirical formula $C_6H_4S_3Se$, the proper name 1,3-dithiole,2-[1-thiol-3-selenol-2-ylidene] and represented by structural formula IV

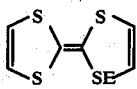 (IV)

may be prepared in accordance with Equation II by reacting an acetylenic compound with a mixture of carbon disulfide and carbon selenide sulfide.

Triselenathiafulvalene, having the empirical formula $C_6H_4Se_3S$, the proper name 1,3-diselenole,2-[1-thiol-3-selenol-2-ylidene] and represented by structural formula V

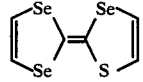 (V)

may be prepared by reacting an acetylenic compound with a mixture of carbon diselenide and carbon selenide sulfide.

Dithiadiselenafulvalene, having the empirical formula $C_6H_4S_2Se_2$, is a generic name for three distinct compounds VI, VII, and VIII, namely:

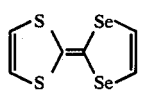 (VI)

1,3-dithiole,2-[1,3-diselenol-2-ylidene]

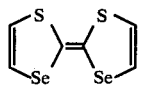 (VII)

1-thiole-3-selenole,2-[1-thiol-3-selenol-2-ylidene]

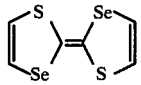 (VIII)

1-thiol-3-selenole,2-[1-selenol-3-thiol-2-ylidene]

Fulvalene compound VI may be prepared by reacting an acetylenic compound with a mixture of carbon disulfide and carbon diselenide, usually in a mole ratio of $CS_2/CSe_2$ of about 4/1 because of the relatively higher reactivity of $CSe_2$ than $CS_2$. Fulvalene compounds VII and VIII are, respectively, cis- and trans-isomers, and may be prepared by reacting an acetylenic compound with carbon selenide sulfide.

Preferred acetylenic starting materials for making the substituted fulvalene compounds include compounds of the general type ZC≡CZ wherein at least one of the Z groups is an electron-withdrawing substituent selected from carboxyl group, carboxyl aliphatic ester groups and amido groups.

Carboxyl and carboxyl aliphatic ester groups suitable as Z substituents may be further defined as members of a class embraced by empirical formula IX:

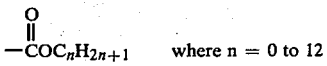 (IX)

with such Z subtituents being attachable to the fulvalene structure at the carbonyl carbon of the Z substituent. Carboxyl group as a Z substituent is typified by carboxyl group contained in formic acid. Carboxyl aliphatic ester groups as the Z substituents are typified by groups contained in the esterification products of formic acid with an aliphatic alcohol of one to about 12 carbon atoms. Representative straight-chain aliphatic alcohols include methyl, ethyl, n-propyl, n-butyl, n-pentyl, n-hexyl, n-heptyl, n-octyl, n-nonyl, n-decyl and n-docecyl alcohols. Representative branched-chain aliphatic alcohols include isopropyl, isobutyl, sec-butyl, tert-butyl, isopentyl, amyl and tert-pentyl alcohols.

Examples of amido group substituted acetylenic compound starting materials include acetylene carboxamide, acetylene dicarboxamide, propiolic carboxamide, propiolic dimethylcarboxamide, acetylene bis(dimethylcarboxamide), propiolic diethylcarboxamide, propiolic dipropylcarboxamide, acetylene bis(diethylcarboxamide), acetylene bis(dipropylcarboxamide), propiolic dioctylcarboxamide and acetylene bis(dinonylcarboxamide).

Particularly preferred acetylenic starting materials for reacting with the $CY_2$ starting material in preparation of the substituted fulvalene compounds are acetylenic-containing compounds such as methyl propiolate, propiolic acid, dimethyl acetylenedicarboxylate and acetylene dicarboxamide. Substituted fulvalene compods prepared from these starting materials will have structures as shown in Equation II with Z substituents selected from the group consisting of hydrogen,

In the reaction of carbon selenide sulfide with methyl propiolate, or with dimethyl acetylenedicarboxylate, or with a mixture of both esters, as the acetylenic starting material, a reaction product may be provided containing one or more intermediate compounds having the structures X:

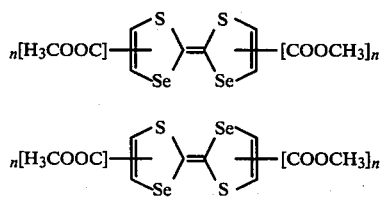

wherein "n" may be 1 or 2. Structures X embrace di, tri, or tetra-ester substituted fulvalene compounds including cis- or trans-isomers of such compounds relative to the substituted ester groups, as well as the cis- and trans-isomers relative to the selenium and sulfur atoms in the rings. Such intermediate compounds may be treated with lithium bromide in the presence of hexamethylphosphoramide to provide the corresponding unsubstituted fulvalene, as suggested in the publication of Lakshmikanthan et al., J. Org. Chem. 41, 882 (1976).

In the reaction of carbon selenide sulfide with propiolic acid as the acetylenic starting material, a reaction product may be provided containing one or more intermediate compounds having the structures XI:

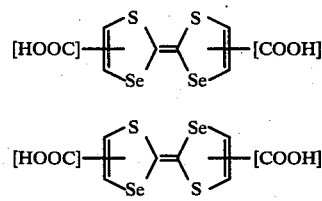

Structures XI enbrace di-substituted fulvalene compounds including the cis- or trans-isomers of such compounds relative to the acid groups, as well as the cis- and trans-isomers relative to the selenium and sulfur atoms. These intermediate compounds may be decarboxylated to the corresponding unsubstituted fulvalene by heating the acid intermediate to 240° C. in pyridine in a sealed vessel, or by treating the acid intermediate with hexamethylphosphoramide in the presence of copper-bronze metal for 20 minutes at 100° C.

In the reaction of carbon selenide sulfide with acetylene carboxamide, or with acetylene dicarboxamide, or with a mixture of both amides, as the acetylenic starting material, a reaction product may be provided containing one or more intermediate compounds having the structures XII:

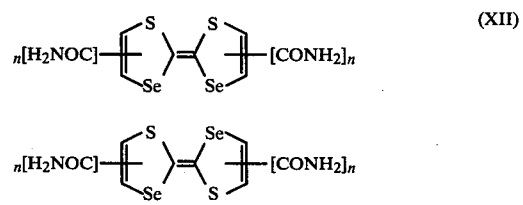

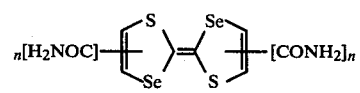

wherein "n" may be 1 or 2. Structures XII embrace di, tri, or tetra-amide substituted fulvalene compounds including cis- or trans-isomers of such compounds relative to the amide groups, as well as the cis- and trans-isomers relative to the selenium and sulfur atoms. Such intermediate amide-substituted compounds may be subjected step-wise to firstly alkaline hydrolysis to form a carboxylate salt of the amide-substituted precursor, which salt is acidified with a strong acid to form a carboxylic acid derivative, which derivative may then be decarboxylated to provide the corresponding fulvalene. Decarboxylation may be accomplished by heating the derivative to 240° C. in pyridine in a sealed vessel, or by treating the derivative with hexamethylphosphoramide in the presence of copper-bronze metal for 20 minutes at 100° C.

It has been found that effective synthesis of substituted sulfur-selenium fulvalene compounds is achieved by a combination of suitable temperature and pressure conditions. For example, when acetylenic compounds and the $CY_2$ starting material are subjected to pressures as high as 4500 atmospheres, synthesis does not go forward at temperatures around 20° C. Generally, reaction temperatures of at least about 60° C. are required, and temperatures in a range from about 60° C. to about 110° C. are preferred; reaction temperatures in a range from about 60° C. to about 90° C. are especially preferred. Reaction temperatures greater than about 120° C. should be avoided inasmuch as unwanted by-products may form at such higher temperatures. While pressures of at least about 1000 atmospheres are generally effective in the described process, reaction pressures of about 2000 atmospheres or greater are preferred.

In order to demonstrate the process of the invention, a series of reactions were carried out under varying conditions of temperature, time and pressure for reaction of various acetylenic compounds with carbon selenide sulfide or with a mixture of carbon disulfide and carbon diselenide. The high pressure reactions were run in Teflon capsule having a three-ml capacity. The capsule was mounted in a steel die equipped with a heating band; pressure was applied with a Clifton 200-ton hydraulic press. Acetylenic compound and carbon disulfide starting materials were obtained from Aldrich Chemical Co., Milwaukee, Wis., and were purified by distillation or recrystallization. Carbon diselenide was synthesized by methods shown in Ives, J. Chem. Soc., 1080 (1947), or was obtained from Alfa Products, Danvers, Mass. Carbon selenide sulfide was prepared from phenyl isothiacyanate and hydrogen selenide by a method modified from methods described in U.S. Pat. No. 2,179,816. Infrared spectra for reaction products dispersed in KBr pellets were recorded on a Perkin-Elmer Model 457 grating IR Spectrophotometer; melting point determinations were made using an electrothermal melting point apparatus.

EXAMPLE I

A starting mixture was prepared by dissolving 0.5 g of methyl propiolate (5.9 mmol) and 0.8 g of carbon selenide sulfide (6.4 mmol) in 5 ml of methylene chloride. A three-ml capacity Teflon reaction capsule was filled with a portion of this starting mixture, there being substantially no free-space above the reaction mixture. Pressure was applied to the contents of the reaction vessel and maintained at 5,000 atm., ±200 atm., for a period of about 15 hours, while the temperature was maintained at about 100° C. The capsule was then allowed to cool to room temperature over a period of about two hours, while the pressure was maintained at about 5,000 atm. The capsule was opened and found to contain a reddish-brown solid material in contact with a small amount of dark brown liquid. The solid material was isolated from the liquid by filtration, washed several times with hexane and then dried under reduced pressure. A brown solid material in an amount of 0.53 g was obtained equivalent to a yield of 82 percent, based upon the amount of methyl propiolate used. This brown material was purified by column chromatography using a silica-packed column eluted with a cyclohexane-benzene mixture. A red solid material was obtained which, when re-crystallized from a benzene-methanol mixture, yielded red crystals having a melting point of 254°–255° C. The purified product was identified as 4,4'(5')-bis(carbomethoxy)diselenadithiafulvalene, as characterized by the following analytical data:

IR peaks: 1710, 1545, 1430, 1250, 1040, 940, 830 and 730 cm$^{-1}$.

Mass spectrum: m/e 416 (based on $^{80}$Se).

EXAMPLE II

The high pressure reaction of methyl propiolate and CSeS was repeated under conditions substantially as set out in Example I, except that the pressure applied was 4,500 atm., and the reaction time was about 14 hours. A dark reddish-brown solid material was obtained in an amount of 0.52 g, equivalent to a yield of 80 percent. Qualitative determinations of the reaction product confirmed the presence of relatively pure compound identified as 4,4'(5')-bis(carbomethoxy)diselenadithiafulvalene.

EXAMPLE III

A starting mixture was prepared by dissolving 0.9 g of dimethyl acetylenedicarboxylate (6.4 mmol) and 0.8 g of carbon selenide sulfide (6.4 mmol) in 5 ml of methylene chloride. Conditions of reaction were repeated substantially as set out in Example I, above, with a pressure of 5,000 atm., ±200 atm., applied to the contents of the reaction vessel, heated to a temperature of about 100° C. for about 10 hours. A reddish-brown solid material was obtained in contact with a red liquid, which solid material was separated by filtration, washed and dried as described before. A brown solid material was obtained in an amount of 0.75 g, equivalent to an 89 percent yield based upon the amount of dimethyl acetylenedicarboxylate used. The material was then purified by column chromatography using a silica-packed column eluted with a cyclohexane-benzene mixture. A red solid material was obtained which when recrystallized from methanol yielded reddish-brown crystals having a melting point of 138° C. (literature m.p. 138° C.). The product, having UV absorption peaks at 250, 290, 325 and 434 nm, was identified as 4,4',5,5'-tetrakis(carbomethoxy)diselenadithiafulvalene.

EXAMPLE IV

The high pressure reaction of dimethylacetylene dicarboxylate and carbon selenide sulfide was repeated under conditions substantially as set out in Example III except that the pressure applied was about 4500 atm., and the reaction time was about 15 hours. A reddish-brown solid material was obtained in an amount of 0.68 g, equivalent to a yield of 85 percent. Qualitative determinations of the reaction product confirmed the presence of relatively pure compound identified as 4,4',4,5'-tetrakis(carbomethoxy)diselenadithiafulvalene.

EXAMPLE V

A starting mixture was prepared by dissolving 0.4 g of propiolic acid (5.7 mmol) in 5 ml of methylene chloride. To this mixture was added 0.8 g of carbon selenide sulfide (6.4 mmol). Conditions of reaction were repeated substantially as set out in Example I, above, with a pressure of 5000 atm., ±200 atm., applied to the contents of the reaction vessel heated to a temperature of about 85° C. for about 12 hours. Upon opening of the reaction vessel after cooling to room temperature, CO$_2$ gas was found to have evolved from the reaction mixture. A brown solid material was removed from the capsule, and then treated sequentially by the steps of washing with hexane, dissolving in 1N NaOH, filtering, acidifying with 2N HCl, and then drying the product overnight under reduced pressure at 60° C. A brown solid material was obtained in an amount of 0.42 g, equivalent to a yield of 70 percent based upon propiolic acid starting material. The product, having a melting point above 330° C. and characterized by IR peaks at 3500–3200, 1680, 1550, and 1390 cm$^{-1}$, was identified as diselenadithiafulvalene-4,4'(or 5')-dicarboxylic acid.

EXAMPLE VI

A starting mixture was prepared by dissolving 0.5 g of acetylene dicarboxamide (4.4 mmol) in 5 ml of dimethyl formamide. To this mixture was added 0.8 g of carbon selenide sulfide (6.4 mmol). A three-ml capacity Teflon reaction capsule was filled with a portion of this starting mixture, there being substantially no free-space above the reaction mixture. Pressure was applied to the contents of the reaction vessel and maintained at 5,000 atm., ±200 atm., for a period of about 12 hours, while the temperature was maintained at about 90° C. After the capsule cooled to room temperature the reaction product was poured into water, from which a fine, brown solid material precipitated. The material was then removed by filtration and washed with small quantities of water and ethyl ether, and then dried under reduced pressure. A brown solid material was obtained in an amount of 0.52 g equivalent to a yield of 80 percent based upon the amount of amide starting material. After recrystallization of the brown material from acetone solvent, a brown solid material was obtained having a decomposition point of about 250° C. The brown product, characterized by IR peaks at 3300, 1660, 1480, 1320, 1180, 1050, 1000, 870 and 720 cm$^{-1}$, was identified as 4,4′,5,5′-tetrakis(carboxamide)diselenadithiafulvalene.

EXAMPLE VII

A starting mixture was prepared by dissolving 0.9 g of dimethyl acetylenedicarboxylate (6.4 mmol), 0.52 g of carbon diselenide (3.0 mmol) and 1.52 carbon disulfide (20.0 mmol) in 5 ml of methylene chloride. Conditions of reaction were repeated substantially as set out in Example I, above, with a pressure of 5,000 atm., ±200 atm., applied to the contents of the reaction vessel, heated to a temperature of about 80° C. for about 12 hours. The capsule was allowed to cool to room temperature over a period of about two hours. A solid material was obtained in contact with a liquid, which solid material was separated by filtration, washed and dried as described before. A reddish solid material was obtained in an amount of 0.72 g. This material, when subjected to thin layer chromatography separation techniques (i.e., silica-covered plates eluted with 60/40 ratio of hexane/methylene chloride), separated into three distinct components. Two of the components were identified as tetracarboxy-substituted tetrathiafulvalene and tetracarboxy-substituted tetraselenafulvalene compounds as indicated by elution retardation factors and infrared spectra. Ultraviolet and infrared spectra of the third component supported its identification as a tetracarboxy-substituted diselenadithiafulvalene, having two sulfur atoms in one ring and two selenium atoms in the other ring.

Although specific examples of the instant invention have been set forth hereinabove, it is not intended that the invention be limited solely thereto, but is to include all the variations and modifications falling within the scope of the appended claims.

What is claimed is:

1. A process for preparing a fulvalene compound, said process comprising the step of subjecting a mixture of reactants to a pressure of at least about 1,000 atmospheres, for a time and at a temperature sufficient to form said fulvalene compound, said mixture of reactants comprising at least one compound selected from a first group consisting of carbon disulfide, carbon diselenide and carbon selenide sulfide, and said mixture of reactants comprising at least one compound selected from a second group consisting of compounds containing an acetylenic moiety of the general formula

ZC≡CZ wherein the Z substituents may be the same or different and are selected from the set consisting of the following members:

wherein R is selected from hydrogen and alkyl, aryl and alkaryl groups of up to about 12 carbon atoms; with the proviso that at least one of the Z substituents is an electron withdrawing group, with the further proviso that said mixture of reactants comprises one or more compounds selected from said first group such that both sulfide and selenide atoms are contained within the ring structure of a fulvalene compound prepared from said mixture of reactants.

2. The process of claim 1 wherein said Z substituent is selected from carboxyl and carboxyl aliphatic ester groups contained in a class defined by the empirical formula

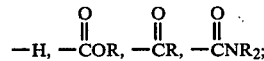

3. The process of claim 1 wherein said compound containing an acetylenic moiety is methyl propiolate, propiolic acid, dimethyl acetylenedicarboxylate, or acetylene dicarboxamide.

4. The process of claim 1 wherein the step of subjecting a mixture of reactants comprising carbon selenide sulfide and methyl propiolate to a pressure of at least about 4,000 atmospheres provides a reaction mixture containing one or more intermediate compounds having the structures

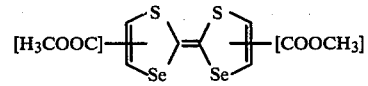

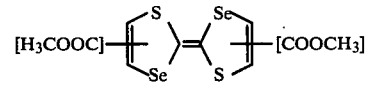

5. The process of claim 4 wherein said intermediate compound is subjected to alkaline hydrolysis to form a salt, which salt may be subjected to acid hydrolysis to form a carboxylic acid derivative, which carboxylic acid derivative may be subjected to decarboxylation to form diselenadithiafulvalene.

6. The process of claim 1 wherein the step of subjecting a mixture of reactants comprising carbon selenide sulfide and propiolic acid to a pressure of at least about 4,000 atmospheres provides a reaction mixture containing one or more intermediate compounds having the structures

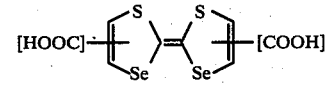

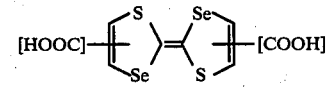

7. The process of claim 6 wherein said intermediate compound is subjected to decarboxylation to form diselenadithiafulvalene.

8. The process of claim 1 wherein the step of subjecting a mixture of reactants comprising carbon selenide sulfide and dimethyl acetylenedicarboxylate to a pressure of at least about 4,000 atmospheres provides a reaction mixture containing one or more intermediate compounds having the structures

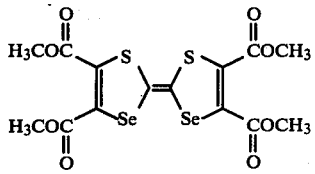

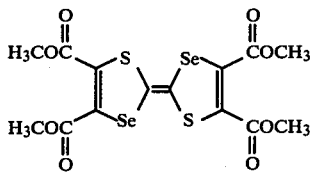

9. The process of claim 8 further characterized by treating said intermediate compound with lithium bromide in the presence of hexamethylphosphoramide to form diselenadithiafulvalene.

10. The process of claim 1 wherein the step of subjecting a mixture of reactants comprising carbon selenide sulfide and acetylene dicarboxamide to a pressure of at least about 4,000 atmospheres provides a reaction mixture containing one or more intermediate compounds having the structures

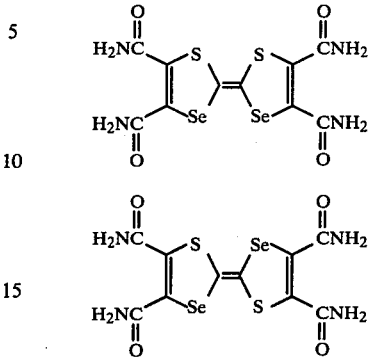

11. The process of claim 10 wherein said intermediate compound is subjected to alkaline hydrolysis to form a salt, which salt may be subjected to acid hydrolysis to form a carboxylic acid derivative, which carboxylic acid derivative may be subjected to decarboxylation to form diselenadithiafulvalene.

12. The process of claim 1 wherein the temperature of said reactants is maintained at about 60° C. or higher.

* * * * *

UNITED STATES PATENT AND TRADEMARK OFFICE
CERTIFICATE OF CORRECTION

PATENT NO. : 4,465,845
DATED : August 14, 1984
INVENTOR(S) : Yoshiyuki Okamoto and Piotr S. Wojciechowski It is certified that error appears in the above-identified patent and that said Letters Patent are hereby corrected as shown below:

In column 3, reaction II, the substituents on the substituted fulvalene product should be Z exclusively, whereas one substituent appears as Y.

Signed and Sealed this

Thirtieth Day of April 1985

[SEAL]

*Attest:*

DONALD J. QUIGG

*Attesting Officer*     *Acting Commissioner of Patents and Trademarks*